United States Patent [19]

Schudy

[11] Patent Number: 4,793,804
[45] Date of Patent: Dec. 27, 1988

[54] ORTHODONTIC BRACKET

[76] Inventor: George F. Schudy, 909 Dairy Ashford, Suite 201, Houston, Tex. 77079

[21] Appl. No.: 95,859
[22] Filed: Sep. 14, 1987
[51] Int. Cl.⁴ .............................................. A61C 7/00
[52] U.S. Cl. ...................................................... 433/8
[58] Field of Search .................... 433/8, 9, 10, 11, 12, 433/13, 14, 15, 16

[56] References Cited

U.S. PATENT DOCUMENTS 3,250,003  5/1966  Collito .................................... 433/9
4,242,085 12/1980  Wallshein ............................. 433/14

Primary Examiner—Robert Peshock
Attorney, Agent, or Firm—Bill B. Berryhill

[57] ABSTRACT

An orthodontic bracket for receiving at least one arch wire may comprise: a base portion adapted for attachment to the outer surface of a tooth and first and second wing portions propecting outwardly from the base portion. Disposed between the two wing portions and opening away from the base portion is a channel for receiving an arch wire. At least one of the channel walls is stepped so as to form two slots of differing widths.

10 Claims, 1 Drawing Sheet

ORTHODONTIC BRACKET

BACKGROUND OF THE INVENTION

1. Field of the Invention

The present invention pertains to orthodontic appliances for correcting teeth malalignment. Specifically, it pertains to an orthodontic bracket for use in combination with arch wires in edgewise appliances.

2. Brief Description of the Prior Art

For many years the most popular, effective, and mechanically sound orthodontic appliances used in correcting imperfections in the alignment of teeth has been the appliance generally referred to as the "edgewise appliance". Although there are several variations of the edgewise appliance, it normally comprises brackets which are attached to each tooth and at least one arch wire which spans the teeth engaging each of the brackets. The arch wire may be affixed to each bracket by connecting wire, resilient band or the like. Examples of various types of brackets may be seen in U.S. Pat. Nos. 3,043,007; 3,193,930; 3,626,593; 4,242,085 and 4,310,306.

Most edgewise brackets include a base portion which is adapted for attachment to the outer surface of the tooth, a rectangular groove or slot for receiving the arch wire and wing portions on each side of the slot so as to provide a means of tying or holding the arch wire in place. The width of the bracket slot is very accurately formed to receive the normal rectangularly cross-sectioned wire in a very precise fit. With such attachment, it is possible to control the inclination of the teeth in three planes of space.

For many years, the width of the slot in edgewise brackets was designed for receiving an arch wire, the cross-sectional height of which was 0.022 of an inch. Such a wire is relatively stiff and exerts an often unnecessary amount of force on the teeth. Consequently, many orthodontists began using edgewise appliances with slots designed to receive arch wires having a height of 0.018 of an inch. Through years of use, it became apparent that the larger dimensioned brackets, when used with small wires, had several advantages: greater range and resiliency of the wires used, and less permanent deformation of the arch wires due to occlusive forces during mastication. However, the loose fit between a larger dimensioned bracket and a small wire results in reduced control of the teeth in certain areas.

In early or intermediate stages of straightening a patient's teeth, it may be desirable, for some of the teeth, to have limited freedom of movement (i.e. a loose fit between the bracket and wire). Consequently, some orthodontists use the large slot bracket (0.022″) and the smaller dimensioned arch wire (0.018″). The loose fit between the smaller dimensioned wire and the larger dimensioned bracket allows the wires to work over a longer period of time, imparting less force. This speeds up the leveling stage of treatment and reduces the number of wires used during treatment. In addition, such a loose fit minimizes the problem of the wires being deformed during mastication. While the loose fit between the smaller wire and the larger appliance is desirable in some situations, it is undesirable in others. As earlier mentioned, the loose fit sacrifices control. In the past, orthodontists were forced to choose between a close fit between the bracket and wire or a loose fit using the larger slot with a smaller wire, losing certain advantages regardless of the choice.

Clinical use has demonstrated that the most efficient appliance would be one which used brackets of at least two different sized slots. Brackets with the smaller dimensioned slots would be attached to the anterior or front teeth and brackets with larger dimensioned slots would be attached to the posterior or back teeth. Thus, the advantages of a loose fit would be provided in the posterior part of the mouth and the advantages of greater control (where it is more needed) would be in the anterior part of the mouth. While this may provide the greatest flexibility in treatment of the anterior and posterior teeth and while it may be the best appliance configuration of the prior art, it still does not offer tight fit/loose fit flexibility for treatment of a particular tooth unless the brackets are changed.

SUMMARY OF THE INVENTION

In the present invention, an orthodontic bracket is provided which will allow the orthodontist to selectively utilize the advantages of both loose and tight fits with small wires. For example, initial treatment may dictate a loose fit at the posterior teeth and a precision fit at the anterior teeth. The bracket provides means of acquiring a precision fit, in the latter stages of treatment, at the posterior teeth as well as the anterior.

The bracket of the present invention comprises: a base portion adapted for attachment to the outer surface of a tooth and first and second wing portions projecting outwardly from the base portion. Disposed between the two wing portions and opening away from the base portion is a channel for receiving an arch wire. The opposing walls of the channel are parallel. At least one of the channel walls may be of a stepped configuration so that two slots are formed. The width of the slot adjacent the base portion is less than the width of the slot at the outer opening thereof. Thus, the channel will accommodate, in the slot nearest its base, a smaller arch wire in a precision manner, or in the slot nearest its opening, in a loose fit.

The bracket of the present invention offers in one bracket the choice of a loose fit or a precision fit with a given rectangular arch wire. For example, an orthodontist may use a small wire with the larger slots during initial treatment. For intermediate treatment, he may use a small wire with large slots (loose fit) on some teeth and small slots (precision fit) on other teeth. In finishing, a small wire may be used with the small slot on all teeth.

Obviously, the present invention offers versatility not previously available in orthodontic brackets of the prior art. It is also much more economical than changing brackets to acquire the same flexibility. The design is both simple to manufacture and use. Other objects and advantages of the invention will be apparent from the specification which follows taken in conjunction with the accompanying drawings.

DESCRIPTION OF THE PREFERRED EMBODIMENTS

Figure 1:
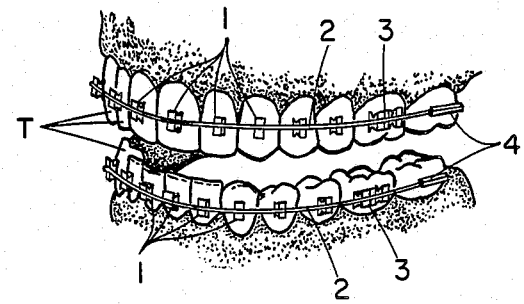
FIG. 1 is a pictorial illustration of the mouth of a person whose teeth are being positioned by an orthodontic edgewise appliance utilizing brackets and an arch wire.

Referring first to FIG. 1, there is illustrated the mouth of a person, whose misaligned teeth T are being corrected by an edgewise appliance, including a plurality of brackets 1 attached to the teeth and engaged by arch wires 2 which engage slots in the brackets as will be more fully understood hereafter. Some of the brackets, such as those illustrated at 3, in the posterior part of the mouth may be double brackets. Usually the terminal teeth are provided with a terminal tube 4 in which the ends of the arch wires 2 may be received. The arch wires 2 are usually rectangular in cross section. Thus, the terminal tubes 4 would be of a corresponding rectangular cross section.

Figure 2:
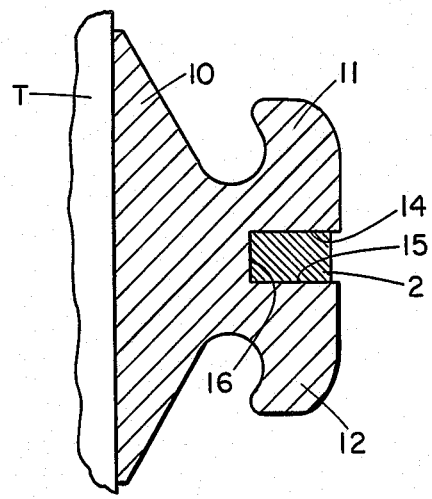
FIG. 2 is a cross-sectional view of an edgewise bracket of the prior art showing its attachment to a tooth and receiving a rectangular arch wire.

Referring now to FIG. 2, there is shown, in cross section, an edgewise orthodontic bracket of the prior art. This type of bracket includes a base portion 10 and first and second wing portions 11 and 12, respectively, projecting outwardly from the base portion 10. The base portion may be bonded to the tooth T. In other cases, the bracket may be attached to a band which encircles the tooth.

The wing portions 11 and 12 have inwardly facing surfaces 14 and 15 which form opposing walls of a slot for receiving the arch wire 2. The arch wire is held in the slot by a wire or elastic band (not shown) attached to the wing portions 11 and 12. The slot walls 14 and 15 terminate at the base portion in a mutually connecting flat surface 16 which forms the base of the slot. As a common example, the width of the slot may be 0.018 of an inch to receive the wire whose height is approximately 0.018 of an inch. This type of precision fit provides the ability to control inclination of the tooth in three planes of space. However, as earlier mentioned, it does not allow selective loose and precision fitting desirable for different stages of treatment.

Figure 3:
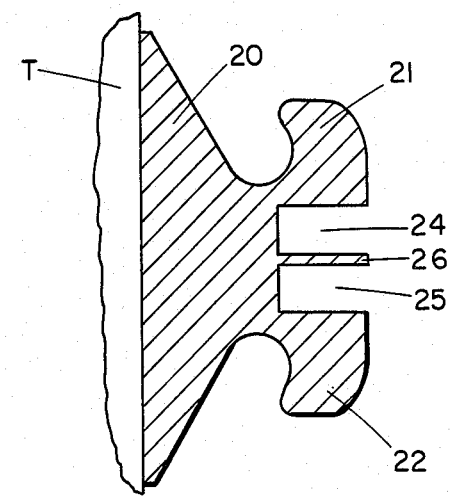
FIG. 3 is a cross-sectional view of another edgewise bracket of the prior art.

Referring now to FIG. 3, there is shown another orthodontic bracket of the prior art. Like the prior art embodiment of FIG. 2, this bracket includes a base portion and first and second wing portions 21, 22. The base portion 20 is attached to the tooth T in any suitable fashion. Between the wing portions 21 and 22 are a pair of slots 24 and 25 separated by an intervening wall 26. In this design, an arch wire may be placed in only one of the slots 24 or 25 during certain phases of treatment and in both of the slots during other phases of treatment, when greater force is required.

Figure 4:
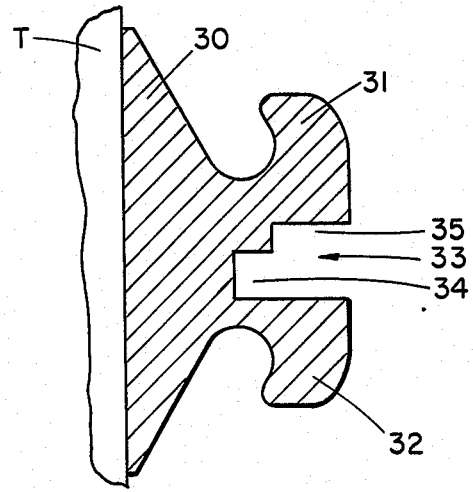
FIG. 4 is a cross-sectional view of the orthodontic bracket according to a preferred embodiment of the invention.
Figure 5:
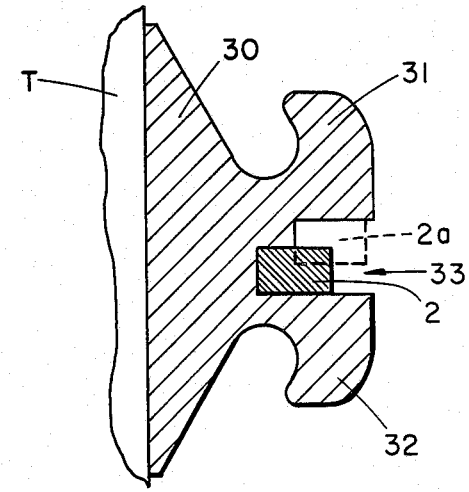
FIG. 5 is a cross-sectional view of the orthodontic bracket of FIG. 4 showing arch wires therein.

Referring now to FIG. 4, a preferred embodiment of the invention is shown which also has a base portion 30 and wing portions 31 and 32. However in this embodiment, a multi-slotted channel 33 is formed between the wing portions. At least one wall of the channel is stepped so that two slots 34 and 35 of differing widths are formed. The width of the slot 34 adjacent the base portion 30 is less than the width of the slot 35 at the outer opening thereof. As shown in FIG. 5, the multi-slotted channel 33 can accomodate an arch wire 2 in a precision fit with the smaller slot 34 or in a loose fit as with arch wire 2a (dotted line) in the larger slot 35.

Thus, the bracket of the present invention is provided with a channel which embodies two communicating slots of differing widths, the smaller being at the bottom of the larger. The side walls of the smaller slot should be parallel. Although the side walls of the larger slot are shown as being parallel, one or both may be inclined so that the opening of the slot is wider than the base. The purpose of this design is to increase the efficiency of the traditional edgewise appliance and/or bracket which normally has only one size slot in each bracket. The dual presence of a large slot 35 and a small one 34 makes it possible for the orthodontist to gradually achieve full bracket engagement without changing arch wires. Full bracket engagement is that point in the mechanotherapy where the arch wire completely fills the slot. This is the point where the appliance has maximum control over the teeth in all three planes of space. Such a graduated engagement significantly reduces patient pain as more gentle forces are produced.

In addition, the bracket of the present invention makes it possible to use smaller slots than ever before (i.e. 0.015 inch) without suffering the disadvantage of restriction in intra bracket space that occurs in the initial phases of orthodontic alignment of teeth. Intra bracket space is the space that occurs around the wire while it is in the channel or slot of the bracket. In the initial correction of teeth that possess malalignment in arch form (in and out) or crookedness (arch length discrepancy) the arch wire forces need to be lighter so that the wire can be deflected into the uneven brackets without too much patient discomfort. When the wire completely fills or begins to approach full bracket engagement, the effective stiffness of the wire is increased because bending within the bracket is restricted. For this reason, the use of a small slot in a traditional edgewise bracket has disadvantages in terms of initial flexibility and alignment.

In summary, the bracket of the present invention will accomodate large and small arch wires, i.e. 0.022×0.028 and 0.014×0.018. It will accomodate a small wire (0.014×0.018, 0.015×0.019, 0.016×0.022) in a "tight fit" good control mode or in a "loose fit" mode. for increased flexibility and decreased forces. Thus, the same bracket may provide good control and/or maximum flexibility, choices not available in the same design of the prior art.

As can now be understood, the orthodontic bracket of the present invention is considerably more versatile than brackets of the prior art offering combined advantages of loose fit arrangements and precision fit arrangements. While a single embodiment of the invention has been described herein, many variations can be made without departing from the spirit of the invention. Accordingly, it is intended that the scope of the invention be limited only by the claims which follow.

I claim:

1. An orthodontic bracket of the edgewise type for cooperation with at least one rectangularly cross-sectioned arch wire comprising: a base protion adapted for attachment to the outer surface of a tooth; first and second wing portions projecting outwardly from said base portion; and a channel formed between said wing portions for receiving said arch wire, said channel having a bottom adjacent said base portion, having side walls and opening away from and in a direction substantially perpendicular to said outer tooth surface, at least one of said side walls being of stepped configuration so that said channel defines at least two adjacent slots of different widths.

2. An orthodontic bracket as set forth in claim 1 in which said stepped configured wall comprises a pair of surfaces substantially perpendicular to said channel bottom and mutually parallel to each other.

3. An orthodontic bracket as set forth in claim 1 in which the width of the first slot nearest said base portion is less than the width of the second slot adjacent thereto.

4. An orthodontic bracket as set forth in claim 3 in which the bottom of said first slot coincides with the bottom of said channel, said first slot opening at the bottom of said second slot.

5. Orthodontic brackets of the edgewise type for straightening a person's teeth in cooperation with a rectangularly cross-sectioned arch wire, each of said brackets comprising a base portion for attachment to the outer surface of one of said teeth, first and second wing portions projecting outwardly from said base portion and a channel formed between said wing portions for receiving said arch wire, said channel being formed by two communicating adjacent slots of differing widths which open in a direction away from and substantially perpendicular to said outer surface of one of said teeth so that said arch wire may simultaneously engage the smaller of said slots in the bracket of one tooth in a tight fit and the larger of said slots in the bracket of another tooth in a loose fit.

6. Orthodontic brackets as set forth in claim 5 in which the smaller of said slots is adjacent said base portion and the larger is at the outer opening of said channel.

7. Orthodontic brackets as set forth in claim 6 in which the bottom of said smaller slot lies at the bottom of said channel, said smaller slot having parallel side walls the upper ends of which terminate at the bottom of said larger slot.

8. Orthodontic brackets as set forth in claim 7 in which one of the side walls of said larger slot is a continuation of one wall of said smaller slot.

9. Orthodontic brackets as set forth in claim 7 in which the side walls of said larger slot are parallel.

10. Orthodontic brackets as set forth in claim 7 in which at least one of the side walls of said larger slot is inclined relative to said parallel side walls of said smaller slot.

* * * * *